(12) United States Patent
Kshirsagar

(10) Patent No.: US 8,139,832 B2
(45) Date of Patent: Mar. 20, 2012

(54) PROCESSING MEDICAL IMAGES OF THE BREAST TO DETECT ANATOMICAL ABNORMALITIES THEREIN

(75) Inventor: Ashwini Kshirsagar, Cupertino, CA (US)

(73) Assignee: Hologic, Inc., Marlborough, MA (US)

( * ) Notice: Subject to any disclaimer, the term of this patent is extended or adjusted under 35 U.S.C. 154(b) by 592 days.

(21) Appl. No.: 12/334,431

(22) Filed: Dec. 12, 2008

(65) Prior Publication Data

US 2010/0150417 A1    Jun. 17, 2010

(51) Int. Cl.
 *G06K 9/00* (2006.01)
(52) U.S. Cl. ........................ 382/128; 382/132
(58) Field of Classification Search ........................ None
 See application file for complete search history.

(56) References Cited

U.S. PATENT DOCUMENTS

| | | |
|---|---|---|
| 5,452,367 A | 9/1995 | Bick et al. |
| 5,572,565 A | 11/1996 | Abdel-Mottaleb |
| 5,729,620 A | 3/1998 | Wang |
| 5,815,591 A | 9/1998 | Roehrig et al. |
| 5,825,910 A | 10/1998 | Vafai |
| 5,917,929 A | 6/1999 | Marshall et al. |
| 6,075,879 A | 6/2000 | Roehrig et al. |
| 6,266,435 B1 | 7/2001 | Wang |
| 6,301,378 B1 | 10/2001 | Karssemeijer et al. |
| 6,434,262 B2 | 8/2002 | Wang |
| 6,901,156 B2 | 5/2005 | Giger et al. |
| 6,956,975 B2* | 10/2005 | Young ........................ 382/263 |
| 7,885,443 B2* | 2/2011 | Zingaretti et al. ............ 382/128 |
| 2008/0021302 A1 | 1/2008 | Kaiser |
| 2008/0144940 A1 | 6/2008 | Russakoff |

OTHER PUBLICATIONS

Hara, T., et. al., "Automated Detection Detection Method for Architectural Distortion Based on Distribution Assessment of Mammary Gland on Mammogram," Int. J. CARS (2006) 1:333-334.

* cited by examiner

*Primary Examiner* — Vinh Nguyen
(74) *Attorney, Agent, or Firm* — Vista IP Law Group LLP

(57) ABSTRACT

Methods, systems and related computer program products are provided for processing a medical image of a breast to detect anatomical abnormalities therein, including anatomical abnormalities that may be associated with breast cancer. The medical image of the breast, which includes a background region bordering a breast tissue region along a skinline thereof, is processed to detect an inward-facing retraction along the skinline, which can be potentially indicative of an anatomical abnormality in the breast tissue. In one preferred embodiment, a display monitor displays first information representative of the medical image of the breast and second information identifying a location of the detected inward-facing retraction on the medical image of the breast. In another preferred embodiment, one or more metrics characterizing the detected inward-facing retraction are used as features in the classification of potential CAD detections in the breast tissue region.

20 Claims, 7 Drawing Sheets

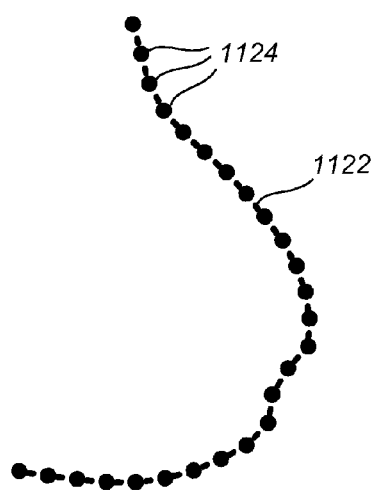
FIG. 11A
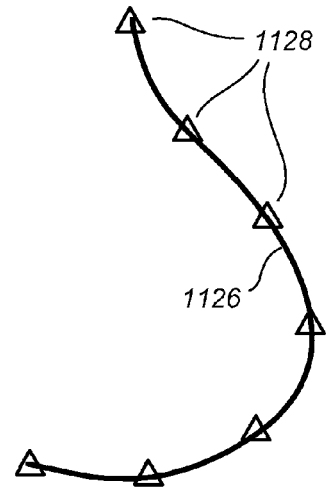
FIG. 11B
FIG. 11C
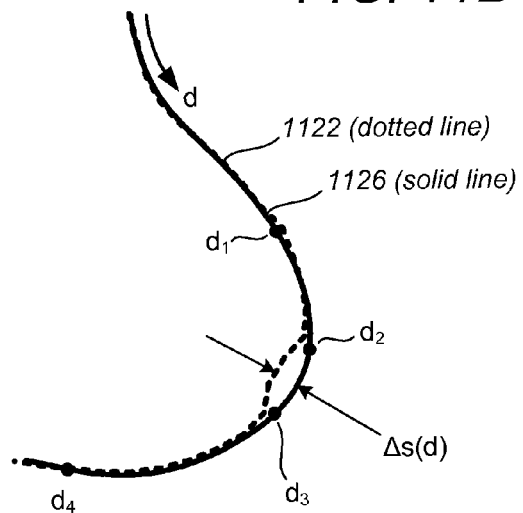
FIG. 11D
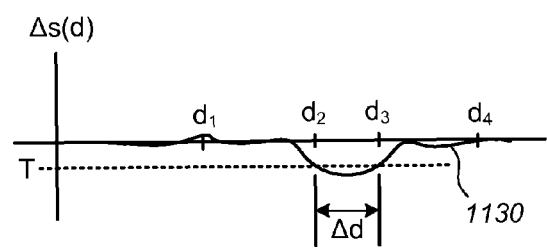

PROCESSING MEDICAL IMAGES OF THE BREAST TO DETECT ANATOMICAL ABNORMALITIES THEREIN

FIELD

This patent specification relates to the processing of medical images of the breast for detecting anatomical abnormalities therein.

BACKGROUND

Breast cancer is the most common cancer among women other than skin cancer, and is the second leading cause of cancer death in women after lung cancer. The American Cancer Society currently estimates that there are about 182,460 new cases of invasive breast cancer per year among women in the United States and 40,480 deaths per year from the disease. Prevention and early diagnosis of breast cancer are of foremost importance. Because early breast cancer does not produce symptoms, the American Cancer Society recommends an x-ray mammogram screening and a clinical breast examination every year for women over the age of 40. Recently, the American Cancer Society has additionally recommended an adjunctive breast MRI (magnetic resonance imaging) screening for women in certain higher-risk groups. Although the preferred embodiments described hereinbelow are particularly applicable and advantageous for use in x-ray mammography and x-ray tomosynthesis breast cancer screening environments, they are also readily applicable for other breast imaging modalities such as breast MRI, breast computed tomography (CT), and breast ultrasound.

Computer-aided detection (CAD) generally refers to the use of computers to analyze medical images to detect anatomical abnormalities in the subject body part. Sometimes used interchangeably with the term computer-aided detection are the terms computer-aided diagnosis, computer-assisted diagnosis, or computer-assisted detection. Upon acquisition of a digital or digitized medical image, a CAD algorithm processes the medical image to detect locations thereon having sufficient likelihood of being associated with an abnormal condition to qualify as a CAD detection, i.e., to qualify as a location on the image that warrants particular attention by a radiologist (or other suitable medical professional) for closer analysis. The CAD algorithm usually identifies a preliminary set of candidate locations in a medical image and then selects which ones, if any, will qualify as actual CAD detections based on a variety of computed features associated with the candidate detections. The CAD results are most often communicated in the form of annotation maps comprising graphical annotations (CAD markers) overlaid on a diagnostic-quality or reduced-resolution version of the medical image, one CAD marker for each CAD detection.

CAD results are mainly used by radiologists as "secondary reads" or secondary diagnosis tools. When analyzing a medical image, the radiologist usually makes his or her own analytical determinations before looking at the CAD results, which either verify those determinations or trigger further inspection of the image. Some CAD implementations have used CAD results in a "concurrent reading" context in which the radiologists look at the CAD results at the same time that they look at the images.

In the field of x-ray mammography, thousands of x-ray mammography CAD systems are now installed worldwide, and are used to assist radiologists in the interpretation of millions of mammograms per year. X-ray mammography CAD systems are described, for example, in U.S. Pat. No. 5,452,367, U.S. Pat. No. 5,572,565, U.S. Pat. No. 5,729,620, U.S. Pat. No. 5,815,591, U.S. Pat. No. 5,917,929, U.S. Pat. No. 6,075,879, U.S. Pat. No. 6,266,435, U.S. Pat. No. 6,301,378, U.S. Pat. No. 6,434,262, and U.S. Pat. No. 6,901,156, each of which is incorporated by reference herein. X-ray mammography CAD algorithms analyze digital or digitized images of standard mammographic views (e.g. CC, MLO) for characteristics commonly associated with breast cancer, such as calcifications, masses, and architectural distortions. CAD systems for use with other modalities such as breast MRI, breast CT, and breast ultrasound imaging are also in various stages of development, although none yet approaches x-ray mammography in terms of widespread acceptance and adoption.

It would be desirable to provide a CAD system for use in breast cancer screening that provides even better performance in the identification of imaged tissue features that may be indicative of a cancerous condition. It would be further desirable to provide a CAD user interface accommodating such improved functionality. Other issues arise as would be apparent to one skilled in the art upon reading the present disclosure.

SUMMARY

Methods, systems, and related computer program products are provided for facilitating the detection of anatomical abnormalities in breast tissue. According to one preferred embodiment, a computer-implemented method is provided comprising the computer-implemented steps of receiving a medical image of the breast, the medical image including a background region bordering a breast tissue region along a skinline thereof, and processing the medical image to detect an inward-facing retraction along the skinline of the breast tissue region that is potentially indicative of an anatomical abnormality in the breast tissue region. First information representative of the medical image is displayed on a display monitor along with second information identifying a location of the detected inward-facing retraction thereon.

Also provided is a computer readable medium embodied with a tangible, non-transitory computer program product that when executed directs a computing apparatus to facilitate the detection of anatomical abnormalities in a breast. The computer program product includes computer code for receiving a medical image of the breast, the medical image including a background region bordering a breast tissue region along a skinline thereof. The computer program product further comprises computer code for processing the medical image to detect an inward-facing retraction along the skinline of the breast tissue region.

Also provided is a computer-aided detection (CAD) system for facilitating the detection of anatomical abnormalities in a breast, comprising a first processor and a first memory associated with the first processor. The first memory stores first instructions that, when executed by the first processor, cause the first processor to perform steps including accessing a medical image of the breast, the medical image including a background region bordering a breast tissue region along a skinline thereof, and processing the medical image to detect an inward-facing retraction along the skinline of the breast tissue region.

BRIEF DESCRIPTION OF THE DRAWINGS

FIG. 11A illustrates a relatively finely constrained contour line associated with the method of FIG. 10;

FIG. 11B illustrates a relatively coarsely constrained contour line associated with the method of FIG. 10;

FIG. 11C illustrates an overlay of the relatively finely constrained contour line of FIG. 11A and the relatively coarsely constrained contour line of FIG. 11B; and FIG. 11D illustrates a separation distance function associated with the method of FIG. 10.

DETAILED DESCRIPTION

Figure 1:
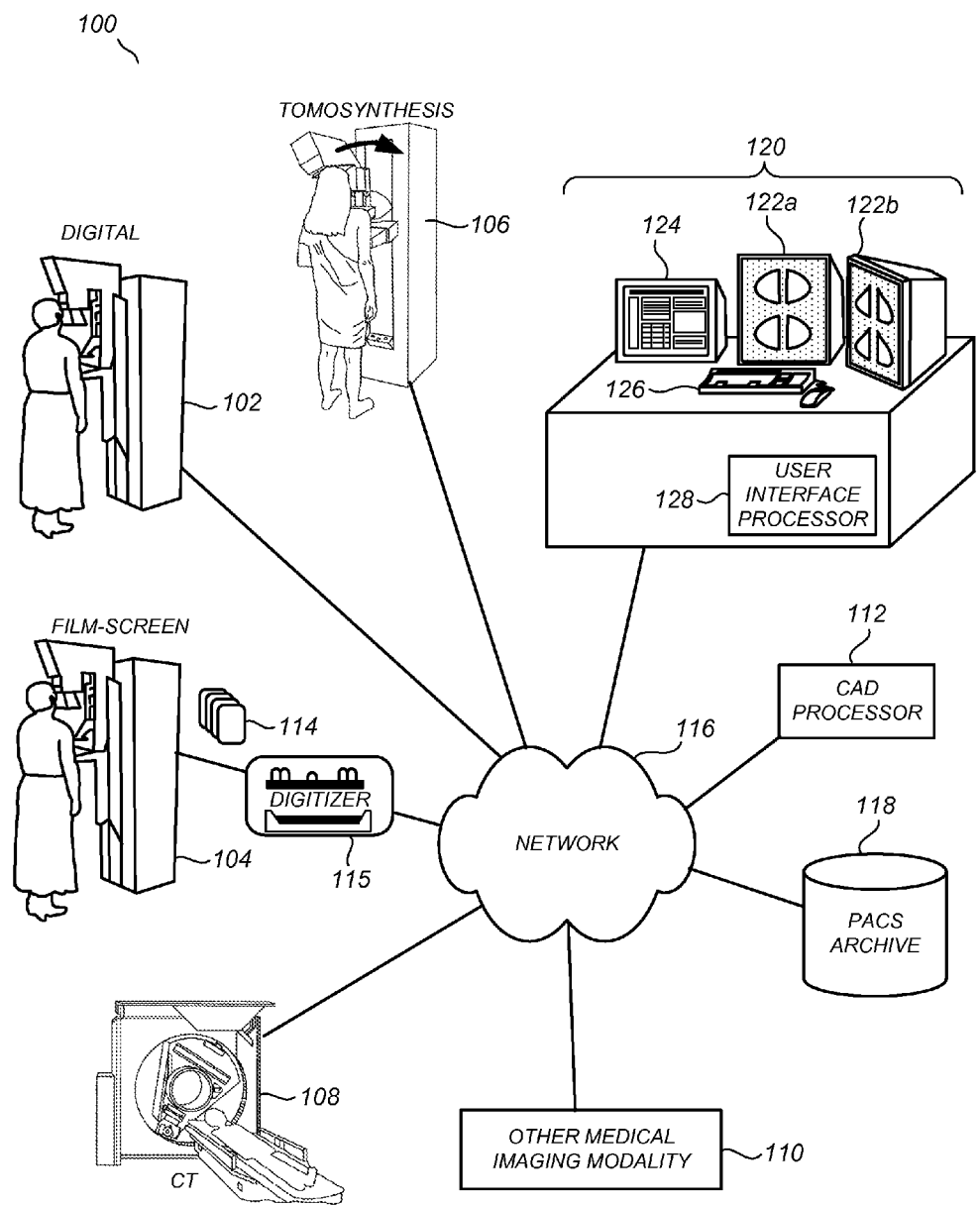
FIG. 1 illustrates a conceptual diagram of a medical imaging environment in which one or more methods can be carried out according to one or more of the preferred embodiments.

FIG. 1 illustrates a conceptual diagram of a medical imaging environment for which one or more of the preferred embodiments is particularly suited. Shown in FIG. 1 is a network 116, which may be a HIS/RIS (Hospital Information System/Radiology Information System) network, to which is coupled a digital mammogram acquisition device 102, a film-screen mammogram acquisition device 104, a tomosynthesis acquisition device 106, a computed tomography (CT) acquisition device 108, and a generalized "other" medical imaging device 110 representative of, for example, magnetic resonance imaging (MRI) acquisition devices and ultrasound acquisition devices. Although described further infra in the context of two-dimensional x-ray mammography images of the breast, one or more methods according to the preferred embodiments are applicable to any breast imaging modality that can yield a two-dimensional projection-style image encompassing a breast skinline and/or a three-dimensional volumetric image from which a two-dimensional slice can be extracted that encompasses a breast skinline. As used herein, skinline refers to the border between a background portion of a breast image, which usually depicts the air or other ambient material surrounding the breast during the imaging procedure, and the internal breast tissue portion of the breast image.

With reference to FIG. 1, a computer-aided detection (CAD) processor 112 coupled to the network 116 receives digital medical images from one or more of the devices 102 and 106-110, and/or from a digitizer 115 that digitizes x-ray mammogram films 114 generated by the film mammogram acquisition device 104. The CAD processor 112 processes the medical images according to one or more of the methods described further infra. A graphical user interface implemented at a review workstation 120 displays the medical images to a viewer in accordance with one or more user interface programs carried out on a user interface processor 128, and further displays graphical markers and/or CAD detections in accordance with one or more of the preferred embodiments described further infra Review workstation 120 comprises a diagnostic display 122, an administrative display 124, and user input devices 126 (e.g., keyboard, mouse, trackball, pointers, etc), under the control of the user interface processor 128. Administrative display 124 is used for input and output of a wide variety of information that may be associated with a particular set of medical images (e.g., listings, tables, plots, text descriptions, etc), as well as for system installation, maintenance, updating, and related tasks.

Preferably, the various medical images and related information are communicated according to the DICOM (Digital Imaging and Communications in Medicine) standard and the network 110 supports the TCP/IP protocol, which is used as the transport protocol for the DICOM standard. Also coupled to the network 110 is a PACS (Picture Archiving and Communication System) archive 118, generally representing a repository for medical information associated with the medical imaging environment, including both current and archived images, current and archived CAD results, radiology reports for completed cases, and so forth.

The preferred embodiments described herein are seamlessly layered upon an existing CAD workflow, in which the digital or digitized medical images are processed by the CAD processor 112, and in which the medical images and their related CAD results are subsequently displayed at the review workstation 120 to a viewer, who makes a clinical determination therefrom. Although one or more of the preferred embodiments is particularly advantageous in the context of en masse breast cancer screening contexts, the clinical determination to be made by the viewer can be in relation to screening, diagnosis, follow-up, or any of a variety of other activities without departing from the scope of the preferred embodiments.

Notably, the medical imaging environment of FIG. 1 is presented by way of example only and is not intended to limit the scope of the preferred embodiments to this particular scenario. By way of example, different combinations of the devices of FIG. 1 can be placed adjacently to each other or integrated into the same hardware boxes without departing from the scope of the preferred embodiments. By way of still further example, the network 110 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments. In view of the present disclosure, a person skilled in the art would be able to implement methods, systems, and/or computer program products capable of achieving the described user interfaces and processing functionalities without undue experimentation, using publicly available programming tools and software development platforms.

Figure 2:
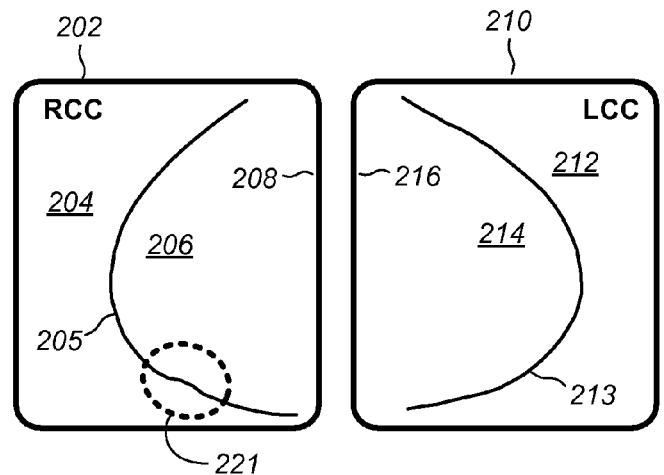
FIGS. 2-3 illustrate conceptual diagrams of x-ray mammogram images including at least one x-ray mammogram image containing at least one anomalous skinline retraction.
Figure 3:
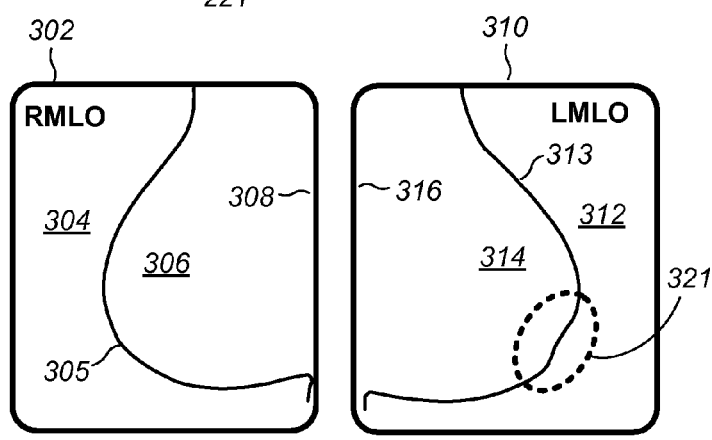

FIGS. 2-3 illustrate conceptual diagrams x-ray mammograms 202, 210, 302, and 310, which can correspond to the same patient or different patients, and which include skinlines 205, 213, 305, and 313, respectively, that are borders between background regions 204, 212, 304, and 312, respectively, and breast tissue regions 206, 214, 306, and 314, respectively. The human female breast has always tended to represent a challenge to the medical imaging field because of its pendulous and generally difficult-to-control nature. For both x-ray mammography and x-ray tomosynthesis environments, the breast is flattened along standardized planes, such as the MLO (mediolateral oblique) and CC (craniocaudal) planes, in order to reduce the required x-ray penetration depth (and thereby reduce the required x-ray radiation dosage), as well as to spread out the tissue to get the best possible look at the fibroglandular structures inside the breast. As a necessary preliminary part of known breast CAD algorithms, the skinline of the breast is identified (segmented) so that the abnormality detection algorithms will be performed only on pixels inside the breast tissue region.

As used herein, references to inward, inner, inside, etc. relative to the skinline refer to that portion of the x-ray mammogram (or other medical image of the breast) containing breast tissue, which is to be contrasted with references to outward, outer, outside, etc., relative to the skinline, which refer to portions of the x-ray mammogram (or other medical image of the breast) representative of space that was outside the breast during the imaging procedure. Although not the case for all imaging modalities and configurations (see, for example, FIG. 7 infra), the portion of the medical image that is inside of the skinline will usually be contiguous with the chest wall of the patient, which is identified by element numbers 208, 216, 308, and 316 in the conceptual diagrams of FIGS. 2 and 3, respectively.

Examples of skinline segmentation algorithms can be found in U.S. Pat. No. 5,452,367 and U.S. Pat. No. 5,572,565, supra. Usually performed in conjunction with skinline segmentation algorithms are nipple detection algorithms that provide the nipple location in the medical image, the nipple location being useful as a reference point for several purposes in CAD processing and/or display. Independently of any CAD processing that is performed (or, optionally, in conjunction therewith), most digital display systems also employ skinline segmentation algorithms in order to amplify the appearance of the skinline in the digital display of the breast. This is done because the amount of x-ray signal attenuation at the skinline itself is very slight compared to the x-ray signal attenuation away from the skinline, because the amount of tissue traversed by the x-ray photons approaches zero at the skinline itself, whereas the amount of tissue traversed by the x-ray photons away from the skinline is usually at least about 3 cm-6 cm. In fact, as discussed in U.S. Pat. No. 5,572,565, supra, in the case of film mammograms that are mounted on light boxes for viewing, a special intensity "hot light" is often needed to help the radiologist locate the skin boundary and the subcutaneous region below it.

One or more of the preferred embodiments described herein are related to a medical observation that inward dimples or retractions of the skinline at or near the nipple can be indicative of a localized shortening of the milk ducts due to the presence of a cancerous condition, which thereby pull the nipple inward. Furthermore, inward retractions of the skinline at locations away from the nipple can be indicative of a shortening or tightening of glandular tissue strands due to the presence of a cancerous condition. Examples of inward skinline retractions that may be indicative of a cancerous condition in the breast tissue are illustrated as elements 221 and 321 in FIGS. 2 and 3, respectively.

Figure 4:
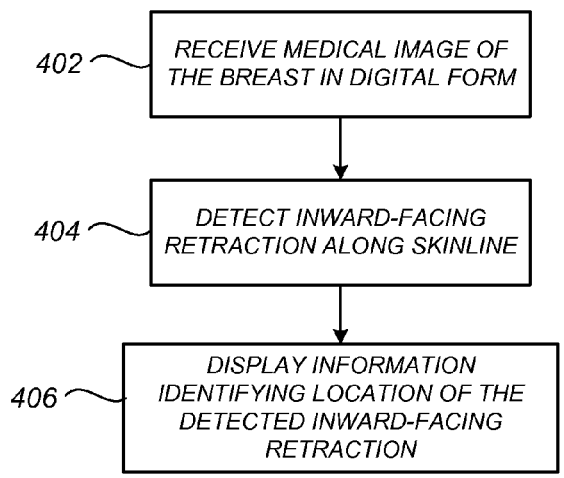
FIG. 4 illustrates facilitating the detection of anatomical abnormalities in breast tissue according to a preferred embodiment.

FIG. 4 illustrates facilitating the detection of anatomical abnormalities in breast tissue according to a preferred embodiment. At step 402, a medical image of the breast in digital form is received. The medical image can be accompanied by information representative of the skinline of the breast that has already been computed by an upstream processing system, or can be processed to segment the skinline therefrom when received. At step 404, the medical image information including the segmented skinline is processed to detect an inward facing retraction along the skinline. At step 406, information is displayed that identifies a location of the inward-facing retraction relative on the medical image.

Figure 5:
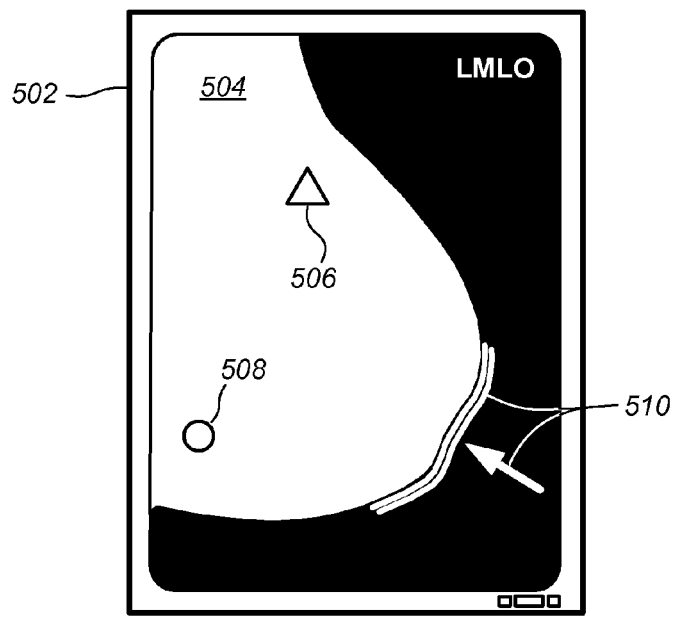
FIG. 5 illustrates an example of a display output according to a preferred embodiment.

FIG. 5 illustrates a graphical display output on a monitor 502 according to a preferred embodiment, comprising an x-ray mammogram view 504 (in this case an LMLO image) upon which is overlaid (or into which is integrated) a skinline retraction marker 510 that visibly highlights the location and shape of the detected inward facing retraction. Although illustrated as highlighting marks along the local skinline contour at the location of the detected skinline retraction, along with an arrow pointing to the center of the retraction, it is to be appreciated that the skinline retraction marker 510 can be implemented in any of a variety of ways (e.g., visual highlighting, audible alarm, text list format, etc.) without departing from the scope of the preferred embodiments. Also illustrated in FIG. 5 are CAD markers 506 and 508 identifying suspected lesions by type and location according to a CAD algorithm performed on the medical image.

For one preferred embodiment, the detection of inward facing retractions such as displayed by skinline retraction marker 510 is performed independently of any CAD algorithm used to detect suspicious lesions inside the breast tissue, and any skinline retraction markers are displayed only as distinct, optional overlays on any CAD-enhanced graphical user interface. Generally speaking, the skinline retractions are not cancerous in themselves, but rather are indicative of a potentially cancerous condition elsewhere in the breast tissue, usually somewhere within the breast tissue near the skinline retraction. For another preferred embodiment (see FIGS. 8-9, infra) the skinline retraction detection algorithm can be integrated into an overall CAD algorithm, such that the classification of candidate CAD detections is influenced at least in part by the presence or absence of any nearby inward skinline retractions.

Figure 6:
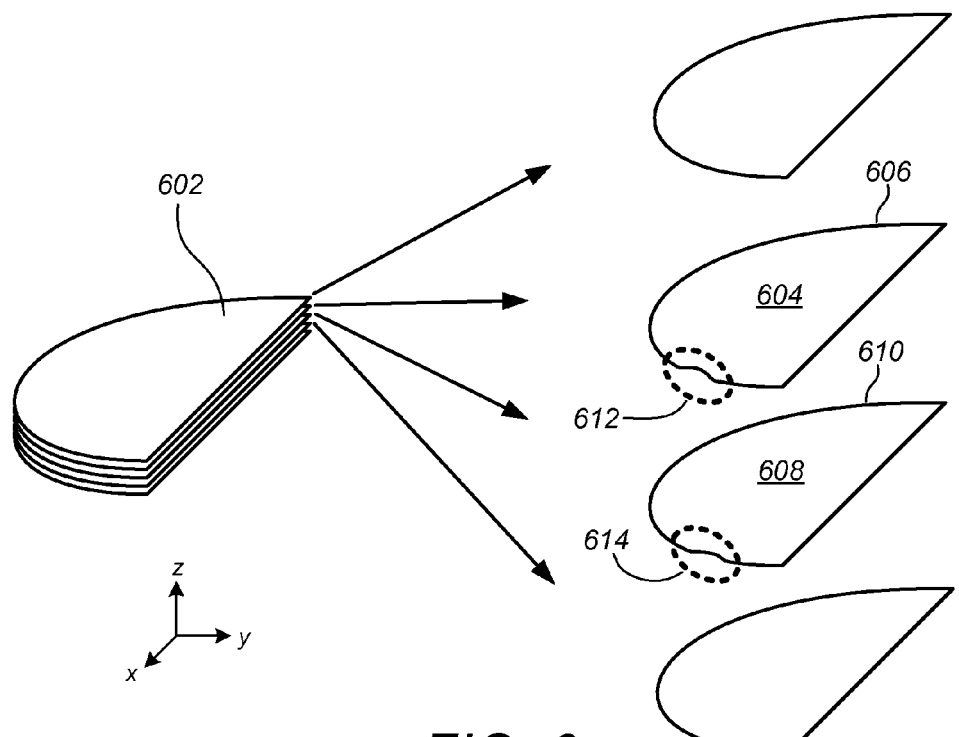
FIGS. 6-7 illustrate conceptual breast image volumes and pluralities of two-dimensional image slices corresponding thereto, including at least one two-dimensional image slice containing at least one anomalous skinline retraction.
Figure 7:
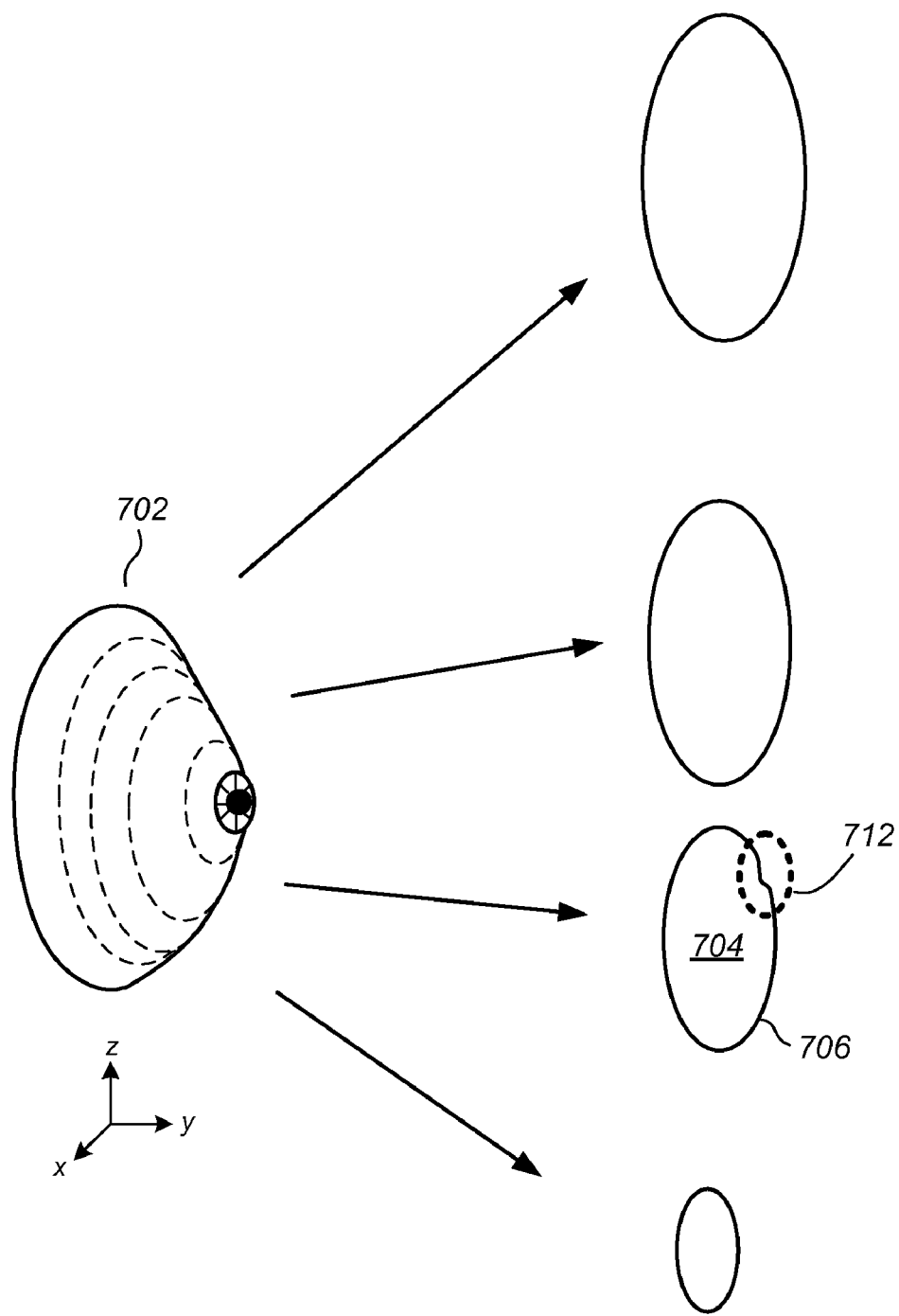

FIGS. 6 and 7 illustrate conceptual breast image volumes and pluralities of two-dimensional image slices corresponding thereto. By way of example, breast image volume 602 may be a backprojected and reconstructed tomosynthesis data set, wherein the breast was compressed by compression paddles along the CC (craniocaudal) compression plane (i.e. parallel to the floor for a patient standing upright in the z-direction). In contrast, breast image volume 702 may be a three-dimensional ultrasound volume of an uncompressed breast of a prone patient, the uncompressed breast extending pendulously into a tub of water or gel while being imaged by a surrounding ultrasound acquisition system.

Inward skinline retraction detection according to one or more of the preferred embodiments can be advantageously applied to image slices derived from either of the image volumes 602 and 702. Thus, FIG. 6 illustrates a first inward skinline retraction 612 detected along a skinline 606 of an image slice 604, and a second inward skinline retraction 614 detected along a skinline 610 of an image slice 608. Optionally, the detected skinline retractions 612 and 614 can be associated with each other by virtue of their spatial proximity in three-dimensional space, with appropriate markings being provided on the graphical user interface and/or appropriate computations being included in CAD routines assessing nearby candidate CAD detections. Similar processing is applicable for the breast image volume 702 of FIG. 7, which illustrates an inward skinline retraction 712 detected along a skinline 706 of an image slice 704. Notably, while many different image slice directions would be applicable for the uncompressed image volume 702 of FIG. 7, it is preferable in the case of the compressed image volume 602 of FIG. 6 for the image slices to be taken substantially parallel to the plane of compression. Otherwise, the bulk of the skinlines for those image slices will be for skin surfaces under direct compression by a compression paddle, which would be less likely to betray a skinline retraction.

Although inward skinline retraction detection according to one or more of the preferred embodiments can be employed the context of either of the image volumes 602 and 702, it has been found particularly advantageous for such inward skinline retraction detection to be performed along skinlines associated with a compressed breast, as is the case for the image volume 602 of FIG. 6. As any woman might testify who has been subjected to conventional x-ray mammography, compression of the breast is a highly unnatural process that contorts the breast tissue in unnatural ways. Referring to the skinline 606 of the image slice 604, there is an artificial "fullness" near that periphery that can be brought about by the compression process, and that "fullness" may result in an increased amount of pulling or "tugging" from underneath the skin surface in comparison to that which would occur if the breast were in an uncompressed, relaxed state. In addition to any three-dimensional imaging modality in which the breast is compressed, inward skinline retraction detection according to one or more of the preferred embodiments can be particularly effective for any two-dimensional imaging modality in which compression is used and in which projection views substantially parallel to the compression plane are acquired, such that a "full" skinline not in direct contact with a compression paddle can be analyzed. Importantly, this class of two-dimensional imaging modalities includes the kind of x-ray mammography that is in widespread use today. Thus, according to one preferred embodiment, inward skinline retractions are detected for a medical image of the breast acquired while the breast is compressed along a compression plane, and wherein the medical image is representative of either (i) a slice of a three-dimensional image volume substantially parallel to the compression plane, or (ii) a projection image acquired in a projection plane substantially parallel to the compression plane.

Figure 8:
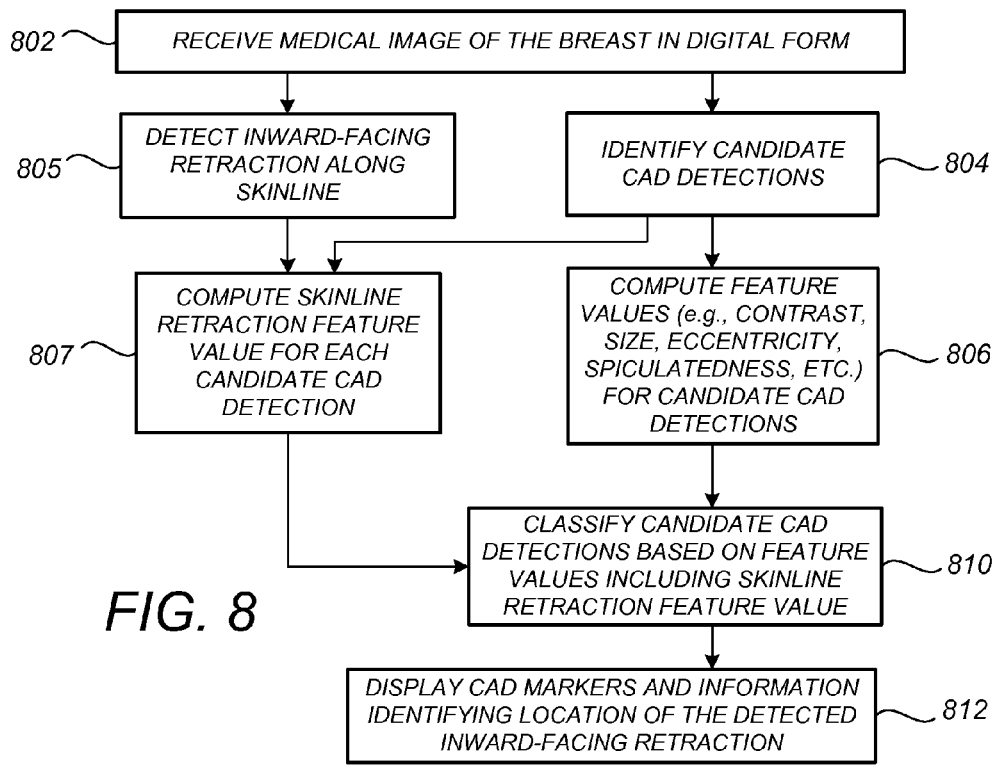
FIG. 8 illustrates facilitating the detection of anatomical abnormalities in breast tissue according to a preferred embodiment.

FIG. 8 illustrates facilitating the detection of anatomical abnormalities in breast tissue according to a preferred embodiment. At step 802, a medical image of the breast in digital form is received. The medical image can be accompanied by information representative of the skinline of the breast that has already been computed by an upstream processing system, or can be processed to segment the skinline therefrom using, for example, one or more methods described in U.S. Pat. No. 5,452,367, supra. It is to be appreciated that U.S. Pat. No. 5,452,367 discusses measuring skin thickening near a detected skinline, which is highly distinguishable from detecting inward skinline retractions according to one or more of the preferred embodiments herein, by virtue of both the different shapes under detection and the different structural mechanisms causing such conditions. With skin thickening, the shape being sought is an elongate two-dimensional solid shape having increases and decreases in width, which can be associated with abnormal growth in subcutaneous fat. In contrast, in detecting inward skinline retractions according to one or more of the preferred embodiments herein, the pattern being sought is a localized inward curvature, which can be associated with an abnormal shortening of milk ducts and/or glandular tissue strands within the breast tissue.

Referring again to FIG. 8, at steps 804 and 806 candidate CAD detections are identified using known methods and various known computed features related thereto are computed, such as area, spiculatedness, margin sharpness, eccentricity, sphericity, average grey level, contrast, cluster characteristics, and breast density characteristics. As used herein, candidate CAD detection refers to a location in the medical image that meets certain preliminary criteria associated with potential anatomical abnormalities according to the CAD algorithm being performed. Based on a plurality of computed features associated with each candidate CAD detection, the candidate CAD detections are then classified by the CAD algorithm, the results of which include a status of each candidate as being either dismissed by the CAD algorithm or marked as an actual CAD detection on the output display. According to a preferred embodiment, at step 805 the medical image information including the segmented skinline is processed to detect an inward facing retraction along the skinline, and at step 807 each of the candidate CAD detections is assigned one or more additional features, termed herein skinline retraction features, that characterize an association (if any) between that candidate CAD detection and each inward skinline retraction (if any) detected at step 805. By way of example and not by way of limitation, one such skinline retraction feature could be a distance to the nearest inward skinline retraction, while another could be the number of inward skinline retractions detected within a predetermined threshold distance, while still another could be a metric characterizing a severity of the nearest inward skinline retraction, and so forth. At step 810 each candidate CAD detection is classified according to its computed feature values including the one or more skinline retraction features, and at step 812 a user output display is provided comprising the medical image with CAD detection markers (if any) and skinline retraction markers (if any) overlaid thereon.

Figure 9:
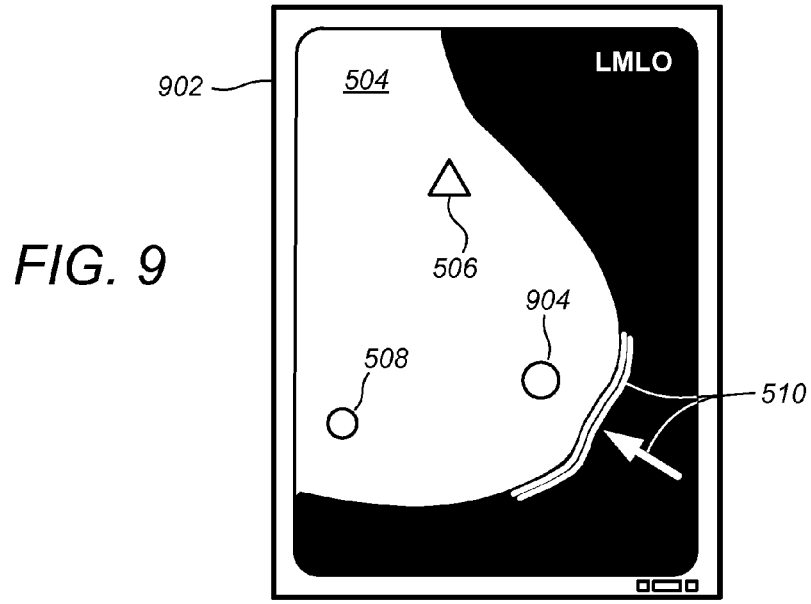
FIG. 9 illustrates an example of a display output according to a preferred embodiment.

FIG. 9 illustrates an example of a display output associated with the preferred embodiment of FIG. 8, and can be contrasted with the display output of FIG. 5, supra, for illustrating a potential advantage of integrating skinline retraction feature values into a CAD algorithm according to one or more of the preferred embodiments. In particular, in a hypothetical scenario associated with FIG. 5 in which skinline retraction detection is provided independently from a CAD algorithm, only the CAD detections 506 and 508 are provided, although the skinline retraction marker 510 is also provided as a cue for the radiologist to more closely examine the breast tissue in the vicinity thereof. However, in a hypothetical scenario associated with FIG. 9 in which skinline retraction features are integrated into the CAD algorithm, an additional CAD marker 904 is provided, reflecting that the skinline retraction features associated with the candidate CAD detection at that location due to the nearby skinline retraction were enough to bump that candidate CAD detection from the "dismissed" category into the "marked" category.

Figure 10:
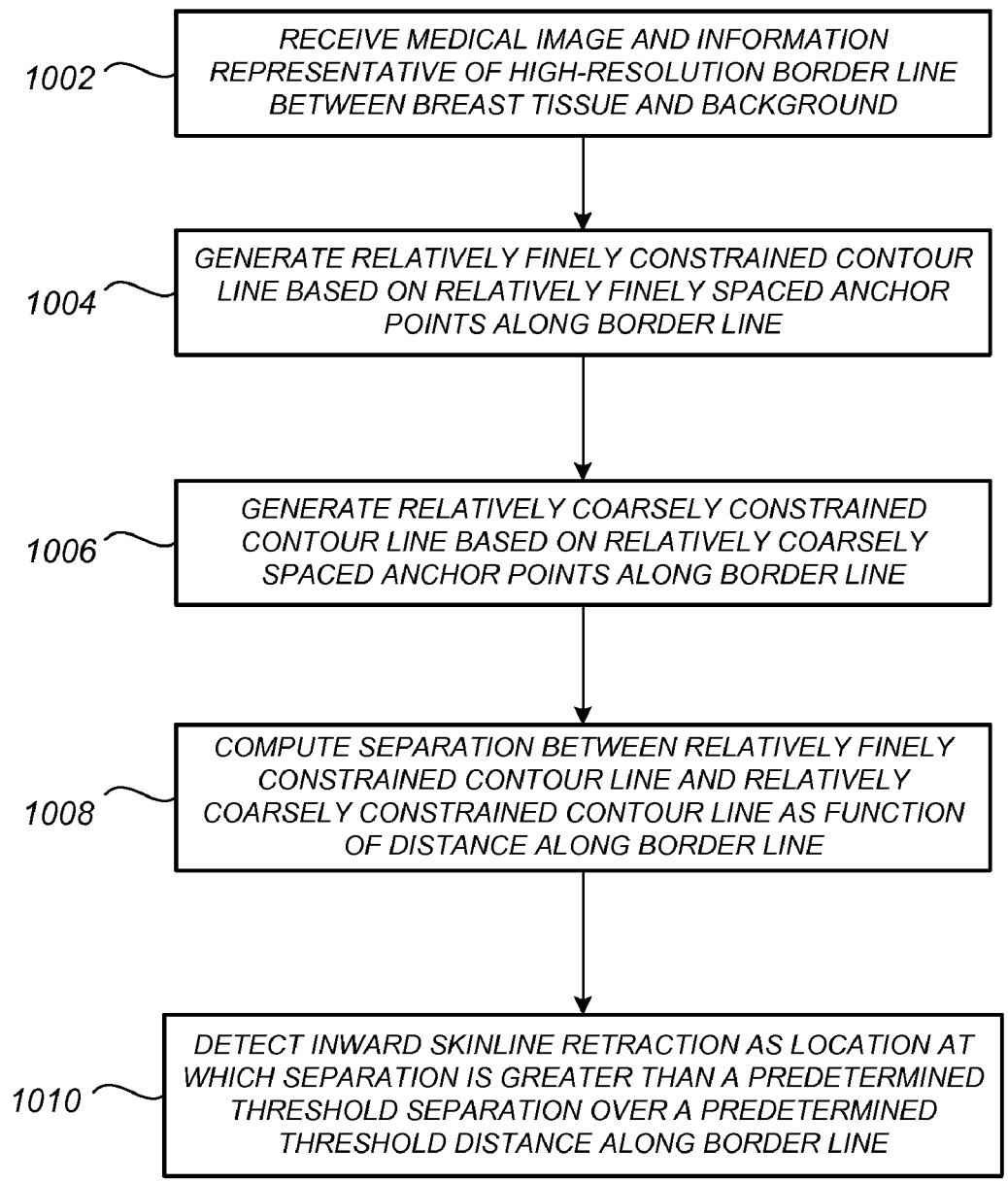
FIG. 10 illustrates detecting an inward-facing retraction along a breast skinline associated with a potential anatomical abnormality in the breast according to a preferred embodiment.

FIG. 10 illustrates detecting an inward-facing retraction along a breast skinline associated with a potential anatomical abnormality in the breast according to a preferred embodiment. FIGS. 11A-11D illustrate conceptual plots by which the method of FIG. 10 may be better understood. It is to be appreciated that although one particularly straightforward way of detecting inward facing skinline retractions is set forth herein in relation to FIGS. 10-11D, any of a variety of different methods for detecting inward facing skinline retractions could be used without departing from the scope of the preferred embodiments.

At step 1002, the medical image is received along with information representative of a high-resolution border line between breast tissue and image background as described supra with respect to step 402 of FIG. 4 and step 802 of FIG. 8. At step 1004, a relatively finely constrained contour line 1122 is generated based on a plurality of relatively finely spaced anchor points 1124 along the skinline. At step 1006, a relatively coarsely constrained contour line 1126 is generated based on a plurality of relatively coarsely spaced anchor points 1128 along the skinline. By way of nonlimiting example, for the particular case of x-ray mammography the finely spaced anchor points can be spaced apart by about 0.6 cm-1.2 cm and the coarsely spaced anchor points can be spaced apart by about 3 cm-5 cm. Several methods are known in the art for computing a relatively finely constrained contour line based on a relatively high number of anchor points, as well as for computing a relatively coarsely constrained contour line based on a relatively low number of anchor points, examples of which can be find in any of a variety of published references such as Press, et. al., *Numerical Recipes in C++: The Art of Scientific Computing,* 2nd Ed., Cambridge University Press, Cambridge UK (2002).

At step 1008, a separation distance function Δs(d) (see FIG. 11D, plot 1130) is computed as a distance between the relatively finely constrained contour line 1122 and the relatively coarsely constrained contour line 1126, with the parameter "d" being a distance along the skinline from an arbitrary starting point. At step 1010, an inward facing retraction is identified as a location along the skinline for which the magnitude of the separation distance function Δs(d) is greater than a predetermined threshold separation T over an interval of at least a predetermined threshold distance Δd along the skinline. By way of example and not by way of limitation, for the particular case of x-ray mammography, one suitable value for the predetermined threshold separation T can be about 0.3 mm and one suitable value for the predetermined threshold distance Δd can be about 2 cm. Other predetermined threshold T values may also be utilized, e.g., about 3 mm-10 mm. Optionally, to further increase the robustness of the algorithm and/or to reduce false positives, steps 1004-1010 can be repeated using different fine and coarse anchor point spacings, different predetermined threshold separations T, and different predetermined threshold distance Δd, with voting or other selection schemes used to select a best result. Thus, for example, according to certain embodiments, at least one of a plurality of predetermined averaging intervals is between about 1 cm-5 cm, and processing the medical image involves detecting an inward-facing retraction by locating a contiguous segment of the skinline having a net average inward concavity or separation distance that is greater than a predetermined threshold T of about 3 mm-10 mm, when evaluated over at least one of a plurality of predetermined averaging intervals along the skinline.

Whereas many alterations and modifications of the preferred embodiments will no doubt become apparent to a person of ordinary skill in the art after having read the foregoing description, it is to be understood that the particular embodiments shown and described by way of illustration are in no way intended to be considered limiting. By way of example, although particular examples of skinline retraction detection are presented supra for two-dimensional x-ray mammogram images and are further disclosed supra in the context of slice-style or projection-style images from other modalities, it is to be appreciated that purely three-dimensional image processing algorithms for detecting skinline retractions in purely three-dimensional volumetric breast images can be used without departing from the scope of the preferred embodiments. In such preferred embodiments the breast tissue region and the background (i.e., non-breast) region are three-dimensional in nature, the skinline is a two-dimensional surface at the border between the breast tissue region and the background region, and the inward skinline elevation retractions are local dimples or valleys in the skinline elevation meeting predetermined criteria. Thus, reference to the details of the described embodiments are not intended to limit their scope, which is limited only by the scope of the claims set forth below.

What is claimed is:

1. A computer-implemented method for facilitating detection of anatomical abnormalities in a breast, comprising the computer-implemented steps of:
    receiving a medical image of the breast, the medical image including a background region bordering a breast tissue region along a skinline thereof;
    processing the medical image to detect an inward-facing retraction along said skinline of the breast tissue region and that satisfies pre-determined criteria, the inward-facing retraction being potentially indicative of an anatomical abnormality within the breast; and
    displaying on a display monitor first information representative of said medical image of the breast and second information identifying a location of said detected inward-facing retraction on the medical image of the breast.

2. The computer-implemented method of claim 1, wherein said second information comprises a graphical overlay that visually highlights said location of said inward-facing retraction on the medical image of the breast.

3. The computer-implemented method of claim 1, wherein said processing the medical image to detect said inward-facing retraction comprises locating a contiguous segment of the skinline meeting predetermined criteria known to be at least partially associated with at least one of a shortening of milk ducts in the breast tissue and a shortening of glandular tissue strands in the breast tissue.

4. The computer-implemented method of claim 1, wherein said processing the medical image to detect said inward-facing retraction comprises locating a contiguous segment of the skinline having a net average inward concavity greater than a predetermined threshold when evaluated over at least one of a plurality of predetermined averaging intervals along the skinline.

5. The computer-implemented method of claim 4, wherein said predetermined threshold is between about 3 mm-10 mm and wherein at least one of said plurality of predetermined averaging intervals is between about 1 cm-5 cm.

6. The computer-implemented method of claim 4, the predetermined criteria comprising a threshold separation between contour lines generated based on respective points along said skinline, the method further comprising:
    generating a relatively finely constrained contour line based on a plurality of relatively finely spaced anchor points along said skinline;
    generating a relatively coarsely constrained contour line based on a plurality of relatively coarsely spaced anchor points along said skinline;
    computing a separation between said relatively finely constrained contour line and said relatively coarsely constrained contour line as a function of distance thereal-ong; and
    identifying said inward facing retraction as a location along said skinline at which said separation is greater than a predetermined threshold separation over a predetermined threshold distance along said skinline.

7. The computer-implemented method of claim 1, wherein said medical image of the breast is an x-ray mammogram.

8. The computer-implemented method of claim 1, wherein said medical image of the breast is a two-dimensional image selected from the group consisting of: an x-ray mammogram, an x-ray tomosynthesis projection image, an x-ray tomosynthesis reconstructed image, a magnetic resonance imaging (MRI) slice, an MRI projection image, an x-ray computed tomography (CT) slice, an x-ray CT projection image, an ultrasound slice, and an ultrasound projection image.

9. The computer-implemented method of claim 7, wherein said medical image results from an imaging procedure in which the breast is compressed along a compression plane, and wherein said medical image is representative of one of (i) a projection image acquired in a projection plane substantially parallel to said compression plane, and (ii) a slice of a three-dimensional image volume substantially parallel to said compression plane.

10. The computer-implemented method of claim 1, further comprising:
processing the medical image to identify at least one candidate CAD detection in the breast tissue region;
computing at least one skinline retraction feature value for each said candidate CAD detection based at least in part on a spatial relationship between said candidate CAD detection and said detected inward-facing retraction; and
classifying each said candidate CAD detection according to a respective plurality of computed feature values including said at least one computed skinline retraction feature value.

11. A non-transitory computer readable medium embodied with a computer program product that when executed directs a computing apparatus to facilitate detection of anatomical abnormalities in a breast, comprising: computer code for receiving a medical image of the breast, the medical image including a background region bordering a breast tissue region along a skinline thereof; and computer code for processing the medical image to detect an inward-facing retraction along said skinline of the breast tissue region and that satisfies pre-determined criteria, the inward-facing retraction being potentially indicative of an anatomical abnormality within the breast.

12. The computer readable medium of claim 11, further comprising computer code for displaying on a display monitor first information representative of said medical image of the breast and second information identifying a location of said detected inward-facing retraction on the medical image of the breast.

13. The computer readable medium of claim 11, further comprising: computer code for processing the medical image to identify at least one candidate CAD detection in the breast tissue region; computer code for computing at least one skinline retraction feature value for each said candidate CAD detection based at least in part on a spatial relationship between said candidate CAD detection and said detected inward-facing retraction; and computer code for classifying each said candidate CAD detection according to a respective plurality of computed feature values including said at least one computed skinline retraction feature value.

14. The computer readable medium of claim 11, wherein said computer code for processing the medical image to detect the inward-facing retraction comprises computer code for locating a contiguous segment of the skinline meeting predetermined criteria known to be at least partially associated with at least one of a shortening of milk ducts in the breast tissue and a shortening of glandular tissue strands in the breast tissue.

15. The computer readable medium of claim 11, wherein said medical image of the breast is a two-dimensional image selected from the group consisting of: an x-ray mammogram, an x-ray tomosynthesis projection image, an x-ray tomosynthesis reconstructed image, a magnetic resonance imaging (MRI) slice, an MRI projection image, an x-ray computed tomography (CT) slice, an x-ray CT projection image, an ultrasound slice, and an ultrasound projection image.

16. A computer-aided detection (CAD) system for facilitating detection of anatomical abnormalities in a breast, comprising:
a first processor; and
a first memory associated with said first processor and storing first instructions that, when executed by said first processor, cause the first processor to perform steps comprising:
accessing a medical image of the breast, the medical image including a background region bordering a breast tissue region along a skinline thereof; and
processing the medical image to detect an inward-facing retraction along said skinline of the breast tissue region and that satisfies pre-determined criteria, the inward-facing retraction being potentially indicative of an anatomical abnormality within the breast.

17. The CAD system of claim 16, further comprising:
a second processor; and
a second memory associated with said second processor and storing second instructions that, when executed by said second processor, cause the second processor to display on a display monitor first information representative of said medical image of the breast and second information identifying a location of said detected inward-facing retraction on the medical image of the breast.

18. The CAD system of claim 16, said first instructions causing the first processor to perform further steps comprising:
processing the medical image to identify at least one candidate CAD detection in the breast tissue region;
computing at least one skinline retraction feature value for each said candidate CAD detection based at least in part on a spatial relationship between said candidate CAD detection and said detected inward-facing retraction; and
classifying each said candidate CAD detection according to a respective plurality of computed feature values including said at least one computed skinline retraction feature value.

19. The CAD system of claim 16, wherein said processing the medical image to detect the inward-facing retraction comprises locating a contiguous segment of the skinline meeting predetermined criteria known to be at least partially associated with at least one of a shortening of milk ducts in the breast tissue and a shortening of glandular tissue strands in the breast tissue.

20. The CAD system of claim 16, wherein said medical image of the breast is a two-dimensional image selected from the group consisting of: an x-ray mammogram, an x-ray tomosynthesis projection image, an x-ray tomosynthesis reconstructed image, a magnetic resonance imaging (MRI) slice, an MRI projection image, an x-ray computed tomography (CT) slice, an x-ray CT projection image, an ultrasound slice, and an ultrasound projection image.

* * * * *